United States Patent [19]

Waite

[11] Patent Number: 4,831,015

[45] Date of Patent: May 16, 1989

[54] HIGH POTENCY BIOMASS-FREE AVOPARCIN AND A METHOD FOR ITS PREPARATION

[75] Inventor: Jack P. Waite, Fareham, Great Britain

[73] Assignee: American Cyanamid Company, Stamford, Conn.

[21] Appl. No.: 84,761

[22] Filed: Aug. 13, 1987

[51] Int. Cl.$^4$ ............................................. A61K 31/71
[52] U.S. Cl. ................................... 514/29; 424/123; 514/37; 514/39; 514/40; 514/770
[58] Field of Search ...................... 514/29, 37, 39, 40, 514/770; 502/62; 424/123

[56] References Cited

U.S. PATENT DOCUMENTS

| | | | |
|---|---|---|---|
| 2,926,085 | 2/1960 | Geerlings | 514/770 |
| 3,152,953 | 10/1964 | Strong et al. | 514/770 |
| 4,485,102 | 11/1984 | Waite | 514/29 |

FOREIGN PATENT DOCUMENTS 627718  9/1961  Canada ............................... 514/770

Primary Examiner—Carl F. Dees
Attorney, Agent, or Firm—John W. Hogan, Jr.

[57] ABSTRACT

The invention relates to high potency biomass-free avoparcin and a method for its preparation.

10 Claims, No Drawings

HIGH POTENCY BIOMASS-FREE AVOPARCIN AND A METHOD FOR ITS PREPARATION

BACKGROUND OF THE INVENTION

Avoparcin is an important, commercially available, antibiotic which is used in the feed of meat-producing animals to accelerate their growth rate. This antibiotic is generally prepared by a fermentation process and consists essentially of two water-soluble glycopeptides, hereinafter referred to as the alpha and beta components of avoparcin. These components are discussed in the following publications: W. J. McGahren, et al., *Structure of Avoparcin Components,* Journal of the American Chemical Society, 102, 1671 (1980) and *Avoparcin,* Journal of the American Chemical Society, 101, 2337 (1979).

When employed as an animal feed additive, avoparcin has generally been administered to said animals, in or with their feed, in the form of an alkyl sulfate complex associated with the dried solid of the whole harvest mash, or biomass, in which it was produced. In practice, this product has been obtained by a process involving, (1) acidification of the antibiotic containing biomass, from the fermentation process; (2) treatment of the acidified mixture with filter aid and alkali metal alkyl sulfate; (3) filtration of the thus treated acidified mixture and (4) drying of the recovered solids which comprise: avoparcin alkyl sulfate complex, filter aid, and biomass. Although the thus prepared product has been utilized effectively for acceleration of the growth rate of animals for nearly a decade without report of any undesirable side effects or toxicity problems, the relatively low potency of this biomass containing product limits, to some extent, the marketability of the antibiotic and the physical forms in which it may be administeeed.

Although the art suggests that avoparcin alkyl sulfate complexes can be obtained in a finished form free of mycelia, unfortunately, the art processes when scaled up to provide the volume of avoparcin alkyl sulfate complex needed by the meat-producing industry are not entirely satisfactory. They are limited by extended filtration periods and consumption of considerable amounts of energy and/or fuel necessary to achieve the degree of drying necessary to provide a dry stable product. Additionally, the physical form and appearance of the avoparcin alkyl sulfate complex produced by the scaled up art process leaves something to be desired.

In general, prior art processes of commercial significance are limited in that the concentration of the active ingredient in the product is limited by the nature of the process and the present state of the fermentation art. The maximum potency of the product which is currently achieved, is in the range 17% to 18%. The concentration of the active ingredient in the product is entirely dependent on the fermentation mash feedstock to the processes and will inevitably vary significantly from batch to batch. It is difficult to specify and quantify the many components, other than the active ingredient, which are present in the products as manufactured by the current processes. Furthermore, both the nature and the relative concentrations of these components will vary from batch to batch. Additionally, the physical and chemical properties of the product as currently produced, imposes major limitations on the types of supplement formulations which can be prepared. U.S. Pat. No. 4,485,102 describes nn improved method for the isolation of avoparcin alkyl sulfate complex of increased potency by adsorption and removal of some of the impurities on a sorptive medium which does not retain the antibiotic.

It is an object of this invention to provide high potency biomass-free avoparcin and a method for its preparation.

SUMMARY OF THE INVENTION

The invention relates to a method for the preparation of high potency biomass-free avoparcin comprising adsorbing avoparcin from aqueous medium under acidic conditions with a montmorillonite clay and treating the avoparcin-rich clay with aqueous base to recover avoparcin.

It has been found that high potency biomass-free avoparcin may be obtained by adsorption of the antibiotic from aqueous medium under acidic conditions, thus removing the antibiotic from the fermentation biomass, and avoiding many of the problems associated with prior processes which rely on removing impurities from the antibiotic.

The process of this invention depends on the availability of an adsorbent which combines the properties of having a suitably high capacity to adsorb avoparcin from aqueous solution under conditions which are compatible with the stability of avoparcin; the ability to recover the avoparcin from the adsorbent by aqueous elution under conditions which avoid possible degradation of the avoparcin; availability at a suitably low cost and preferably can be recycled to the process; and also preferably has a specific gravity of at least two to allow for separation of the adsorbent from the spent fermentation mash, including the mycelial solids, by differential cenrrifugation.

Surprisingly, it has been found that naturally-occurring and chemically modified clays having montmorillonite unit cell structure, which are commonly referred to as montmorillonite, satisfy the above requirements. Montmorillonite clays, in either natural or chemically modified forms, adsorb 8% to 12% by weight of avoparcin from aqueous solution under acidic conditions. The avoparcin may be readily recovered from these adsorbents by aqueous alkaline elution and preferably at a pH of 10.5 to 10.8, and further that the adsorption capacity of the montmorillonites for avoparcin does not deteriorate on multiple re-use. These clays may be described as hydrous sodium and/or calcium, magnesium aluminum silicates having the montmorillonite unit cell structure of two silicon-oxide sheets with an aluminum hydroxide sheet sandwiched between them. Montmorillonite is described as having a Si-Al-Si structure. Montmorillonite clays suitable for use in the method of this invention are commercially available in various forms: calcium form, sodium form, and a calcium form which has been activated to varying degrees by treatment with acid. Typically the average composition of these clays on a weight basis is in a range of about 50% to 65% $SiO_2$, 10% to 20% $Al_2O_3$, 2% to 4% MgO, 3% to 4% CaO and 0.2% to 4% $Na_2O$., recognizing of course that these ranges are averages and fluctuations due to processing, treatments or natural variation are common. Preferred montmorillonite adsorbents for use in the method of this invention typically have a surface area of 70 to 240 $M^2/g$ and a pH which is measured as a 2% aqueous suspension in a range of about pH 3 to pH 11. These montmorillonite clays are commonly known as bentonite or Fullers earth and are readily available in large volumes. Commercially available montmorillonite clays include Volclay ® Wyoming Bentonites, VEE-GUM ®, Panther Creek ®, Brebent, Surrey Powder, and Fulmont, many of which are available in a variety of grades.

While the above-discussion refers to the antibiotic avoparcin, other antibiotics which can be prepared as complexes are the basic antibiotics such as BM 123, BM 123 gamma, gentamycin, vancomycin, streptomycin and neomycin. These antibiotics can be prepared by disclosed fermentative biosynthetic techniques and converted to their respective complexes by the process essentially as described above for the preparation o avoparcin alkyl sulfate complexes. The problems encountered in the preparation and use of said antibiotics and their complexes are, however, essentially identical to those encountered in the manufacture and use of the avoparcin and its complexes. Likewise, improvements in the process for the preparation of the above-identified antibiotics are applicable thereto.

In practice the method of this invention may be carried out by acidifying the avoparcin fermentation mass with a mineral acid and preferably sulfuric acid. In the avoparcin-containing fermentation mash a pH 1.9 to 2.3, has been found to be the optimum pH for adsorption by montmorillonite. At this pH range 93% to 95% of the avoparcin content is present in solution in the aqueous phase, the remainder being held in the mycelial solids. The resulting acidified fermentation mash is then preferably processed in one of the two following ways:

1. The acidified mash may be then filtered by any suitable means, e.g., rotary vacuum filtration, to recover a mash acid filtrate which is free of the fermentation biomass (mycelial solids and nutrient solid residues).

This filtrate is then treated with the adsorbent for a sufficient period of time to optimize adsorption which is usually in a range of one-half to one hour and if necessary, the pH of the suspension of adsorbent in the filtrate is readjusted to 1.9 to 2.3 using sulfuric acid. The avoparcin adsorbent may then be isolated by filtration.

2. Alternatively and more preferably, the avoparcin can be adsorbed directly from the acidified aqueous whole fermentation mash. In this process the adsorbent is added and the pH readjusted to 1.9 to 2.3 and this mixture is agitated for a sufficient period of time to optimize adsorption which is usually in the range of one-half to one hour. The avoparcin-rich adsorbent is then separated from the spent fermentation mash, including the biomass, by differential centrifugation using a suitable design of solid bowl centrifuge. Such a separation is possible in practice because of the relatively high specific gravity of the adsorbent (2.5) compared with that of the mycelial solids present in the fermentation mash (approximately 1).

Adsorption from the whole fermentation mash has two significant advantages:
 a. It avoids the necessity of filtering the fermentation mash and the cost associated with this; and
 b. The avoparcin present in the spent mash separated, 5% to 7% of that present in the starting mash, can also be recovered by spray drying to produce conventional biomass-containing feed intermediate, so increasing the overall process recovery.

The optimum quantities of montmorillonite absorbent for use in the method of this invention has been determined to be in a range of 8 g to 15 g adsorbent/1 g avoparcin. The amount of adsorbent employed is dependent on the sorptive capacity of the particular aadsorbent, the particle size of the adsorbent, and the process option employed. Preferred adsorbent usage for process option 1 above (adsorption from mash acid filtrate) is optimized in a range of 8 g to 10 g/g of avoparcin in the filtrate depending upon the adsorbent which is used. While preferred adsorbent usage for process option 2 above (adsorption from whole fermentation mash) is optimized in a range of 13 g to 15 g/g avoparcin.

It is recognized that greater quantities of adsorbent would of course also be effective and that the above preferred adsorbent use levels represent minimum quantities to obtain optimization of the productivity of the processes and maximization of the antibiotic recovery, while minimizing costs, effluents and materials handling.

The avoparcin is readily recovered from the avoparcin-rich adsorbent obtained by either method by aqueous elution under alkaline conditions. The optimum pH for elution is 10.5 to 10.8 and the maximum concentration of avoparcin in the eluent which can be achieved in practice is about 25 to 30 g/liter.

Thus the rich adsorbent is suspended in water and the pH of the slurry adjusted to 10.5 to 10.8 by the addition of a suitable alkali such as sodium hydroxide solution, sodium carbonate solution or preferably, aqueous ammonia solution. The slurry is then filtered by any suitable method, e.g., centrifuge, filter press, etc. and the primary eluant recovered. To achieve complete recovery, the filter cake may then be subjected to washing with a suitable volume of alkaline water, preferably dilute aqueous ammonia solution. The resulting secondary eluant can then be combined with the primary eluant for further processing.

If the eluant so recovered is sprayed dried directly, the product obtained usually contains about 50% to 55% avoparcin, as the montmorillonite also adsorbs various materials from the fermentation mash in addition to the avoparcin. These materials are co-eluted with the avoparcin.

To further purify the eluant prior to spray drying and so increase the potency of the product, it is possible to subject the eluant to membrane filtration (ultra-filtration), since a major proportion of the "impurities" present in the eluant are of lower molecular weight than the avoparcin. These impurities may be removed by using a membrane with a molecular weight cut-off in the range of 1500 to 2000, making it possible to achieve significant purification. Product potencies after spray drying of 90% are obtainable by this procedure.

Although a number of techniques are possible for the isolation of the product from the eluant either directly or after purification by membrane filtration, spray drying is preferred. To obtain a powder of reasonably high bulk density, it is preferable to concentrate the eluant feedstock. It has been found that it is possible to increase the avoparcin content in the eluant to over 150 g/liter by thin film evaporation.

The product obtained by the process described above is of a cream to pale fawn in color and readily soluble in water to give a solution of pH 6 3 to 6.5. These processes are illustrated diagrammatically in the Drawing. The invention is further illustrated by the following non-limiting examples.

EXAMPLE 1

Capacity of various mineral adsorbents to adsorb avoparcin from an aqueous solution of avoparcin sulphate Avoparcin sulphate (11 g 'as is') is dissolved in 500 mL of distilled water. The resulting solution is assayed at 18.2 g/L avoparcin by high performance liquid chromatography and has a pH of 3.9.

Portions of this solution (25 mL) are treated with a 2.5 g portion of each of a selection of commercially available adsorbents. The suspensions are shaken at ambient temperature for 30 minutes to equilibrate. The suspensions are then filtered and the avoparcin content of the filtrate determined by HPLC. The results of these experiments which are summarized in Table I below demonstrate the superiority of monmmorillonite clays for adsorbing avoparcin from solution.

TABLE I

| Adsorbent | % Avoparcin adsorbed from solution | % Concentration avoparcin on adsorbent |
|---|---|---|
| Sodium montorillonite, (Brebent, Laporte Earths) | 98.5 | 17.9 |
| Calcium montmorillonite, acid, activated (Fulmont AA, Laporte) | 84.7 | 15.4 |
| Attapulgite, (Attasorb LVM, Lawrence Chemicals) | 51.0 | 9.3 |
| Synthetic Clay, (Celkate T-21, Johns-Manville) | 41.1 | 7.5 |
| China Clay (English China Clays) | 20.8 | 3.8 |
| Titanium dioxide, anatase (Tiona WDB, Laporte) | 12.4 | 2.25 |
| Cellulose powder (Clar-o-cel, CECA) | 10.7 | 1.95 |
| Kieselguhr (Type G, Merck) | 5.5 | 1.0 |
| Hydroxylapatite (BDH) | 4.9 | 0.9 |

EXAMPLE 2

Adsorption of avoparcin from a filtrate of the fermentation mash by sodium montmorillonite To a 4 L portion of an avoparcin fermentation mash is added 80 g of filter aid (Dicalite 478). To the stirred mash is slowly added 98% sulphuric acid to a pH in the range of 1.9 to 2.1. The acidified mash is filtered using a pre-coated vacuum filter to recover a mash acid filtrate assaying at 18.9 g/L avoparcin by HPLC.

Portions of this filtrate (500 mL) are treated with the sodium montmorillonite adsorbent (Fulbent 570, Laporte Earths, Ltd) and the pH re-adjusted to the appropriate pH with sulphuric acid. After stirring for 30 minutes at 18° C., the suspensions are filtered and the filtrates assayed for avoparcin content by HPLC. The results of these experiments are summarized in Table II below.

TABLE II

| pH of treatment | Adsorbent level % w/v acid filtrate | | | | |
|---|---|---|---|---|---|
| | 11 | 12 | 13 | 14 | Mean |
| 2.2 | 89.8 | — | 94.6 | — | 92.2 |
| 2.1 | — | 91.7 | — | 95.4 | 93.55 |
| 2.0 | 91.4 | — | 94.7 | — | 93.05 |
| 1.9 | — | 92.6 | — | 95.4 | 94.0 |
| Mean | 90.6 | 92.15 | 94.65 | 95.4 | — |

EXAMPLE 3

The effect of the pH on the adsorption of avoparcin from a fermentation mash filtrate by sodium montmorillonite A portion of avoparcin production fermentation mash is treated with 2% w/v of Filteraid (Dicalite 478) and the pH slowly adjusted to 2.1 with 98% sulphuric acid. The acidified mash is filtered using a pre-coated vacuum filter to recover the mash acid filtrate assaying at 21.1 g/L avoparcin by HPLC.

Portions of this filtrate (250 mL) are treated with 20 g of the sodium montmorillonite adsorbent (Fulbent 570, Laporte Earths Ltd). The pH of the stirred suspension is adjusted by the addition of either 98% sulphuric acid or solid $NaHCO_3$. After stirring for 30 minutes at ambient temperature, the suspensions are filtered and the avoparcin content of the filtrate determined by HPLC. The results of these experiments are summarized in Table III below.

TABLE III

| pH of treatment | % Avoparcin adsorbed from the mash filtrate |
|---|---|
| 1.9 | 69.1 |
| 2.8 | 67.7 |
| 3.8 | 64.4 |
| 4.9 | 64.8 |
| 5.8 | 60.4 |
| 6.9 | 38.8 |
| 7.6 | 10.8 |

EXAMPLE 4

Preparation of biomass-free avoparcin intermediate by adsorption from fermentation mash filtrate A portion of avoparcin production fermentation mash is treated with 2% w/v of Dicalite 478 and the pH adjusted to 2.1 with 98% sulphuric acid. The acidified mash is filtered using a pre-coated vacuum filter to recover the mash acid filtrate. The filtrate assayed at 17.48 g/L avoparcin by HPLC.

Five liters of this filtrate is treated with 150 g of Celkate T-21 at pH 2.0, the suspension filtered and the filtrate residue displacement washed with 450 mL of water at pH 2.0. The filtrate (5.3 L) recovered has an avoparcin content of 16.36 as determined by HPLC.

To 5.25 L of this filtrate is added 650 g of the natural calcium montmorillonite (Surrey powder, Laporte Earths Ltd). The pH of the suspension is 3.3 and this is reduced to 2.0 by the addition of 98% sulphuric acid. The suspension is aged with stirring for 15 minutes and the rich adsorbent recovered by vacuum filtration. The spent filtrate assayed at 1.32 g/L avoparcin by HPLC.

The wet adsorbent filter cake is suspended in 2 L of water and the pH adjusted to 10.8 with 36% aqueous ammonia solution. The suspension is filtered to recover 2.155 L of primary eluant assaying at 27.24 g/L avoparcin.

The filter cake is resuspended in 1 L of water and the pH adjusted to 10.8 as before. Filtration yields 1.160 L of the secondary eluant assaying at 10.53 g/L avoparcin.

Finally, the cake is resuspended in 0.5 L of water and again adjusted to pH 10.8. Filtration yields 0.55 L of tertiary eluant assaying at 5.42 g/L avoparcin.

The three eluant fractions are combined to give a solution assaying at 19.31 g/L avoparcin and with a total solids content of 45.55 g/L. A portion of this eluant is spray dried using a mini-spray drier using an air inlet temperature of 200° C./air outlet temperature of 98° C. The product obtained assays at 40.4% avoparcin by HPLC.

Based upon these results, the following process step efficiencies are calculated:

|  | % |
|---|---|
| Mash acid filtrate/Celkate treated filtrate | 99.2 |
| Celkate treated filtrate/rich adsorbent | 92.0 |
| Rich adsorbent/eluant | 93.5 |
| Eluant/spray dried product | 95.3 |
| Overall mash acid filtrate/dry product | 81.3 |

EXAMPLE 5

Preparation of biomass-free avoparcin intermediate by adsorption from fermentation mash filtrate A mash acid filtrate is prepared from a portion of production avoparcin fermentation mash as described in Example 4. The filtrate contains 17.47 g/L avoparcin as determined by HPLC.

The filtrate is treated with 25 g/L of Celkate T-21 at pH 2.0 ($H_2SO_4$) and clarified to yield a treated filtrate assaying at 16.31 g/L avoparcin.

Three parallel preparations are carried out using three different forms of montmorillonite, A Sodium montmorillonite (Brebent);
B. Natural calcium montmorillonite (Surrey powder);
C. Acid activated calcium montmorillonite (Fulmont 300C).

All of the above supplied by Laporte Earths Ltd.

Portions of each adsorbent, 216 g, i.e., 12% w/v, are added to each of 1800 mL of the mash filtrate and the pH of the suspension adjusted to 2.0 with 98% sulphuric acid. After stirring for 15 minutes, the suspension is filtered by vacuum filter and the spent filtrate assayed for avoparcin content by HPLC.

Each wet rich adsorbent filter cake is then subjected to a double reslurry elution at pH 10.5, the pH being adjusted with 36% aqueous ammonia solution. The volumes of water used for the reslurries are:

| Primary elution | 900 mL |
|---|---|
| Secondary elution | 400 mL |

A portion of the primary eluant is spray dried in a minispray drier using an air inlet temperature of 200° C./air outlet temperature of 95° C.

The results for the three preparations are summarized in Table IV below.

TABLE IV

|  | Type of adsorbent | | |
|---|---|---|---|
|  | A | B | C |
| HPLC assay, g/L |  |  |  |
| Spent mash filtrate | 0.84 | 1.15 | 1.26 |
| Primary eluant | 22.2 | 23.4 | 24.7 |
| Secondary Eluant | 9.3 | 9.8 | 8.6 |
| % recovery avoparcin |  |  |  |
| Mash acid filtrate/adsorbent | 94.9 | 92.9 | 92.3 |
| Adsorbent/eluant | 92.2 | 96.5 | 98.2 |
| Overall mash filtrate/dry product | 87.5 | 89.6 | 90.5 |

Avoparcin recovery across the spray drier is essentially quantitative in all cases. The potencies of the dry products obtained from the primary eluant are as follows:

TABLE IV-continued

|  | Type of adsorbent | | |
|---|---|---|---|
|  | A | B | C |
| % avoparcin 'd.b.' | 60.5 | 67.6 | 66.6 |

EXAMPLE 6

The direct adsorption of avoparcin from the fermentation mash using calcium montmorillonite A 500 g portion of an avoparcin production fermentation mash is diluted with 250 g water and 100 g of calcium montmorillonite adsorbent added (Surrey powder, Laporte Earths). The pH is then adjusted to 2.2 by the addition of 98% sulphuric acid.

The rich adsorbent is separated from the spent mash by centrifugation in a tube centrifuge. The centrifugation is carried out for 2 minutes at 1,000 rpm. The supernatant is decanted, assayed for avoparcin content and the suspended solids content determined.

Two experiments are carried out as above using two different batches of production fermentation mash. The results of these experiments are summarized in Table V below.

TABLE V

|  | Fermenter mash batch no | |
|---|---|---|
|  | 1322 | 1324 |
| Assay of mash, g/kg | 24.09 | 25.47 |
| % of avoparcin in aqueous phase | 91.4 | 92.5 |
| Suspended solids content, g/kg | 54.6 | 58.6 |
| Assay spent mash, g/kg | 1.31 | 1.16 |
| Assay spent mash filtrate, g/kg | 0.10 | 0.13 |
| Suspended solids content, g/kg | 36.2 | 26.4 |
| % recovery mash/centrifuge residue | 94.0 | 95.6 |
| Avoparcin concentration on adsorbent | 10.3 | 11.05 |

EXAMPLE 7

Use of a centrifugal decanter for the separation of montmorillonite adsorbent from fermentation mash A separation trial is carried out using a model P600 Super-D-canter manufactured by Pennwalt Ltd.

The feedstock is prepared as follows:
115 kg of production avoparcin fermentation mash, assay 19.7 g/kg is treated with 25 kg of acid activated calcium montmorillonite (Fulmont 300 C, Laporte Earths Ltd). The pH is then adjusted to 2.2 with 98% sulphuric acid.

Portions of this feedstock are passed to the decanter at a range of feed rates and samples of the centrate examined for avoparcin content and suspended solids content.

A series of 5 runs are carried out and the results are summarized in Table VI below.

TABLE VI

|  |  | Centrate | |
|---|---|---|---|
| Run No | Feed rate L/minute | Assay g/kg | Suspended Solids g/kg |
| 1 | 0.5 | 0.78 | 35.4 |
| 2 | 4 | 1.67 | 59.5 |
| 3 | 8 | 1.64 | 66.9 |
| 4 | 8 | 1.61 | 64.8 |
| 5 | 12 | 1.55 | 72.7 |

At the optimum feed rate of about 8 L/minute the adsorbent sludge discharged by the decanter contained 49% solids. The results of this trial confirm the feasibility of achieving satisfactory separation of spent mash from the rich adsorbent on a production scale.

EXAMPLE 8

Elution of avoparcin from calcium montmorillonite

A portion (750 g 'as is') of the sludge recovered by the differential centrifugation experiment described in Example 7, containing 49% solids and an avoparcin content of 42 g/kg on an 'as is' basis, is reslurried with 300 g water.

Aqueous ammonia solution (100 g of 36%) is added and the slurry aged with stirring for 15 minutes. The primary eluent is recovered by vacuum filtration. The filter cake is displacement washed with 300 mL of dilute aqueous ammonia solution (50:1 diluted 36% aqueous ammonia) and the secondary eluant recovered.

A second displacement wash of the dilute aqueous ammonia (300 mL) is then applied, and the resulting tertiary eluant was retained for use as the first displacement wash in the next elution run.

This procedure is repeated for a series of 5 experiments and the results are summarized in Table VIII below.

TABLE VII

| Experiment | pH primary elution | Eluant fraction | g eluant recovered | Assay eluant g/kg | g Avoparcin in eluant |
|---|---|---|---|---|---|
| 1 | 10.3 | 1 | 452.7 | 43.69 | 19.78 |
|   |      | 2 | 332.0 | 36.81 | 12.22 |
|   |      | 3 | 314.1 | — | — |
| 2 | 10.8 | 1 | 499.2 | 41.41 | 20.67 |
|   |      | 2 | 341.5 | 26.50 | 9.05 |
|   |      | 3 | 315.5 | — | — |
| 3 | 10.6 | 1 | -495.2 | 42.08 | 20.84 |
|   |      | 2 | 334.8 | 29.64 | 9.92 |
|   |      | 3 | 310.6 | — | — |
| 4 | 10.5 | 1 | 469.4 | 43.02 | 20.19 |
|   |      | 2 | 330.1 | 36.40 | 12.02 |
|   |      | 3 | 306.2 | — | — |
| 5 | 10.6 | 1 | 488.3 | 41.93 | 20.47 |
|   |      | 2 | 334.5 | 32.26 | 10.79 |
|   |      | 3 | 304.3 | 6.97 | 2.12 |
| Total g avoparcin recovered: | | | | | 158.07 |
| Total g input in adsorbent sludge: | | | | | 157.5 |

The eluant fractions recovered are combined and the product isolated by spray drying in a two-meter diameter chamber pilot machine using nozzle atomization.

Air inlet temperature 250° C./air outlet temperature 100° C. The product assayed at 52%. Avoparcin recovery across the drying step is essentially quantitative.

EXAMPLE 9

Direct adsorption of avoparcin from fermentation mash using acid activated calcium montmorillonite; the effect of recycling spent adsorbent A series of experiments are carried out to examine the effect on process efficiency of recycling the spent adsorbent.

For the first experiment of the series, the procedure is as follows:

A 500 g portion of avoparcin production fermentation mash is diluted with 100 g water and the pH adjusted to 1.9–2.1 by the addition of 98% sulphuric acid.

Calcium montmorillonite (150 g) adsorbent (Fulmont 300 C, Laporte Earths Ltd) are added and the suspension aged with stirring for 15 minutes.

The avoparcin-rich adsorbent is separated from the spent mash by centrifugation using a tube centrifuge. The centrifuge residue is re-suspended in water to give 800 g of slurry which is then subjected to a second centrifugal separation to complete removal of the mycelial solids from the adsorbent.

The centrifuge residue is then reslurried to 500 g in water and the pH adjusted to 10.6 with 36% aqueous ammonia solution.

Five mL of a 0.1% w/v solution of polyacrylamide A150 flocculant are added to aid filtration. Filtration is carried out on a vacuum filter to recover the primary eluant. The filter cake is then subjected to displacement washing with 2×150 mL portions of dilute aqueous ammonia solution to give secondary and tertiary eluant fractions. The tertiary eluant is recycled to become the first displacement wash in the next preparation in the series.

The final spent adsorbent is retained for recycle to the next experiment in the series.

The subsequent experiments in the series used the same procedure except that:

a. the spent adsorbent from the previous experiment is used with a 15 g addition of fresh calcium montmorillonite (Fulmont 300C);
b. after addition of the adsorbent it is necessary to re-adjust the pH to 2.3 with 98% sulphuric acid;
c. the first displacement wash during the elution step uses the tertiary eluant recycled from the previous experiment.

A series of 12 experiments are carried out. The overall results for the series are as follows:

|   | g Avoparcin |
|---|---|
| Total mash input | 135.1 |
| Total available in aqueous phase | 128.8 |
| Lost to spent mash | |
| 1 | 11.1 |
| 2 | 2.4 |
|   | 13.5 |
| Total recovery in eluant | 116.0 |
| % efficiency mash/eluant | 85.9 |

There is no deterioration in the adsorption efficiency or in the filterability of the elution slurry through the series.

The final dry weight of adsorbent recovered is 174.5 g.

What is claimed is:

1. A method for the preaaration of high-potency biomass-free antibiotic avoparcin, BM 123, BM 123 gamma, gentamycin, vancomycin, streptomycin or neomycin comprising adsorbing the antibiotic from an aqueous medium under acidic conditions with a montmorillonite clay, and treating the antibiotic-rich clay with aqueous base to recover said antibiotic.

2. A method according to claim 1 wherein the antibiotic is avoparcin and the montmorillonite clay is a naturally occurring or chemically modified sodium montmorillonite, calcium montmorillonite; or a mixture thereof.

3. A method according to claim 2 wherein the montmorillonite clay has a surface area for a range of 70 to 240 m$^2$/g. and. a pH measured as a 2% by weight aqueous suspension in a range of about pH 3 to pH 11.

4. A method according to claim 3 wherein montmorillonite clay is added to a filtered acidified fermentation mash filtrate which is free of fermentation mash solids; or an acidified aqueous whole fermentation mash, containing avoparcin while maintaining the pH in a range of pH 1.9 to pH 2.3.

5. A method according to claim 4 wherein from 8 grams to 15 grams of montmorillonite clay is added for each gram of avoparcin to be recovered.

6. A method for the preparation of high potency bio-mass free avoparcin comprising acidifying the avoparcin whole fermentation mash with a mineral acid to a pH in a range of pH 1.9 to pH 2.3;

adding a sufficient quantity of a montmorillonite clay to the acidified whole fermentation mash or to the fermentation mash filtrate obtained by filtration of the whole mash;

agitating the mixture for from one-half to one hour, while maintaining a pH of pH 1.9 to pH 2.3;

isolating the avoparcin-rich adsorbent by filtration or differential centrifugation;

treating the avoparcin-rich adsorbent with aqueous base at a pH in a range of pH 10.5 to pH 10.8;

separating the adsorbent by filtration;

isolating high-potency bio-mass free avoparcin by spray drying the avoparcin containing basic filtrate directly or by spray drying of the avoparcin containing basic filtrate which has been subjected to ultra-filtration through a membrane having a molecular weight cut-off in the range of 1500–2000.

7. A method according to claim 6 wherein the montmorillonite clay is a naturally occurring or chemically modified sodium montmorillonite; calcium montmorillonite; or a mixture thereof.

8. A method according to claim 7 wherein the montmorillontte clay has a surface area for a range of 70 to 240 M$^2$/g and a pH measured as a 2% by weight aqueous suspension in a range of about pH 3 to pH 11.

9. A method according to claim 8 wherein from 8 grams to 15 grams of montmorillonite clay is added for each gram of avoparcin to be recovered.

10. A method according to claim 9 wherein the mineral acid is sulfuric acid and the base is aqueous ammonia.

* * * * *